US00PP20669P3

(12) United States Plant Patent
Burton

(10) Patent No.: US PP20,669 P3
(45) Date of Patent: Jan. 26, 2010

(54) ***HEBE* PLANT NAMED 'SUNSET BOULEVARD'**

(50) Latin Name: *Hebe hybrid*
Varietal Denomination: Sunset Booulevard

(76) Inventor: Stephen Burton, 1896 Hamilton Road, Cambridge (NZ)

( * ) Notice: Subject to any disclaimer, the term of this patent is extended or adjusted under 35 U.S.C. 154(b) by 0 days.

(21) Appl. No.: 12/011,336

(22) Filed: Jan. 25, 2008

(65) Prior Publication Data

US 2008/0148440 P1 Jun. 19, 2008

(51) Int. Cl.
*A01H 5/00* (2006.01)

(52) U.S. Cl. ..... Plt./251
(58) Field of Classification Search ..... Plt./251
See application file for complete search history.

(56) References Cited

PUBLICATIONS

UPOV–ROM GTITM Plant Variety Database Feb. 2008 GTI Jouve Retrieval Software search for 'Sunset Boulevard'.*

* cited by examiner

*Primary Examiner*—Annette H Para
(74) *Attorney, Agent, or Firm*—Penny J. Aguirre

(57) ABSTRACT

A new cultivar of *Hebe* hybrid origin, *Hebe* 'Sunset Boulevard', characterized by its abundant flower spikes of mauve pink flowers, dark green foliage, and resistance to powdery mildew.

2 Drawing Sheets

Botanical classification: *Hebe* hybrid.
Cultivar designation: 'Sunset Boulevard'.

BACKGROUND OF THE INVENTION

The present invention relates to a new and distinct cultivar of *Hebe,* botanically of hybrid origin and known as *Hebe* 'Sunset Boulevard' and will be referred to hereafter by its cultivar name, 'Sunset Boulevard'.

The new cultivar derived from a controlled breeding program developed by the inventor at his nursery in Cambridge, New Zealand. The overall objective of the breeding program is to obtain unique selections of *Hebe* plants with desirable flower color, plant form and disease resistance. 'Sunset Boulevard' was selected in February 2004 as a single plant derived as a whole plant mutation resulting from a cross made in January 2003 between the female parent *Hebe* 'Icing Sugar' (unpatented) and either 'Wiri Vogue' or 'Wiri Joy' (both unpatented) as the male parent.

Asexual reproduction of the new cultivar was first accomplished by the inventor using terminal stem cuttings in Cambridge, New Zealand in March 2004. It has been determined that the characteristics of this cultivar are stable and are reproduced true to type in successive generations.

SUMMARY OF THE INVENTION

The following traits have been repeatedly observed and represent the characteristics of the new cultivar, which in combination distinguish 'Sunset Boulevard' as a new and distinct cultivar of *Hebe.*

1. 'Sunset Boulevard' produces numerous flowering racemes per plant; 15 to 20 per plant grown in a 2.5-liter container.
2. 'Sunset Boulevard' exhibits flowers that are mauve-pink in color.
3. 'Sunset Boulevard' exhibits leaves that are dark green in color.

4. 'Sunset Boulevard' exhibits increased mildew resistance in comparison to other cultivars grown by the inventor.

'Sunset Boulevard' differs from its female parent, 'Sugar Icing', in having an increased number of flower spikes that are shorter and wider and comprised of mauve pink flowers. The flowers of 'Sugar Icing' open pink and turn white for a bi-colored effect. 'Sunset Boulevard' differs 'Wiri Vogue' (possible male parent), in having a greater number of flower spikes, flowers that are deeper pink in color, and smaller leaves. 'Sunset Boulevard' has flowers that are similar in color to those of 'Wiri Joy' (possible male parent), however, 'Sunset Boulevard' differs in having a great number of flower spikes and leaves that are less elongated.

BRIEF DESCRIPTION OF THE DRAWING

The accompanying colored photographs illustrate the overall appearance and distinct characteristics of the new *Hebe.* The photographs were taken of a plant approximately 35 weeks in age as grown in a 2.5-liter container outdoors in Cambridge, New Zealand.

The photograph in FIG. 1 provides a view of the blooming habit of 'Sunset Boulevard' and the photograph in FIG. 2 provides a close-up view of the flowers and foliage of 'Sunset Boulevard'.

Figure 1:
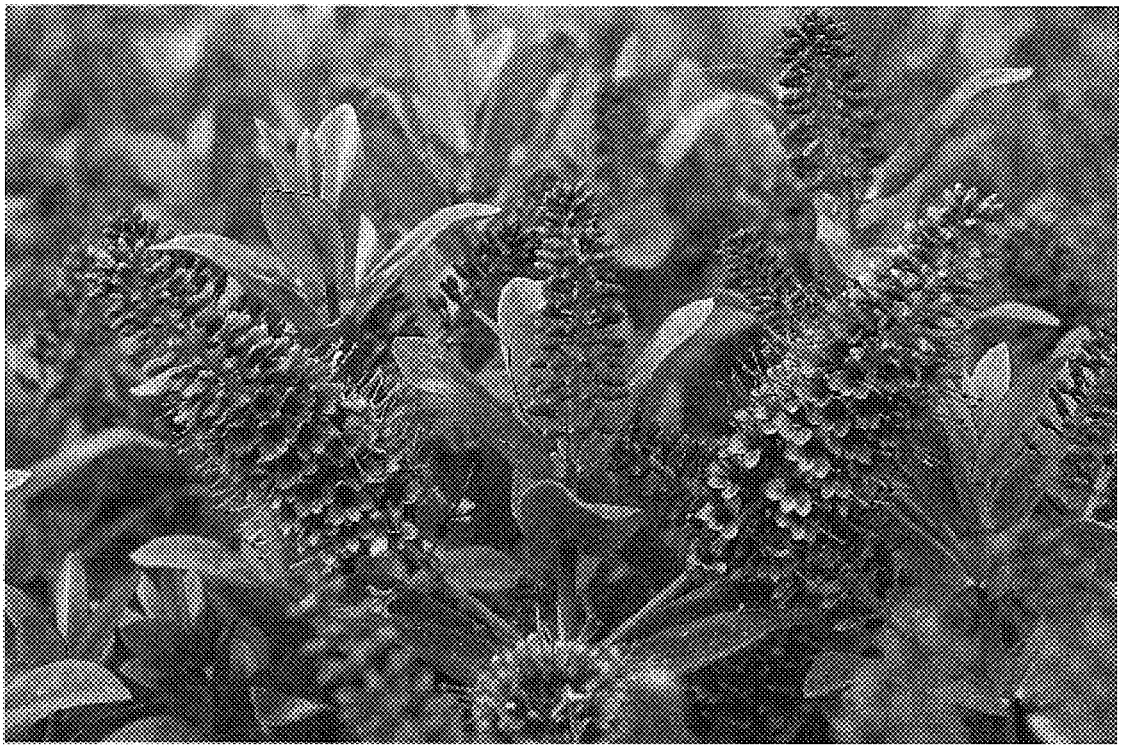
Figure 2:
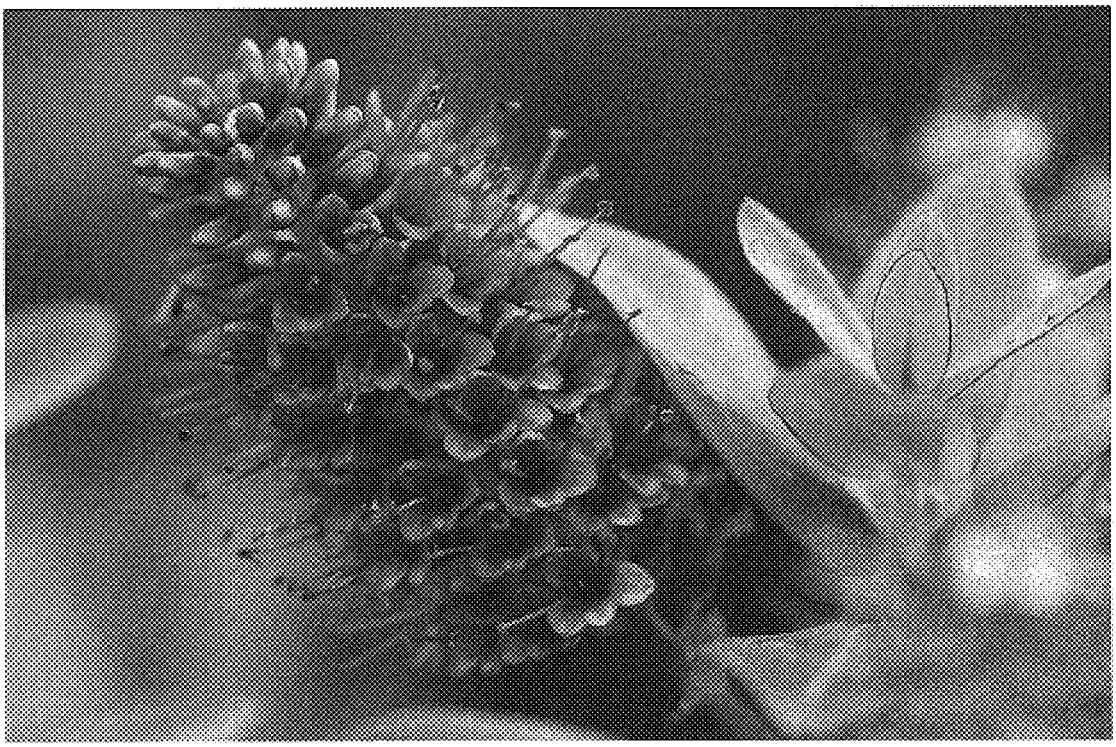

The colors in the photographs are as close as possible with the photographic and printing technology utilized. The color values cited in the detailed botanical description accurately describe the colors of the new *Hebe.*

DETAILED BOTANICAL DESCRIPTION OF THE PLANT

The following is a detailed description of plants of the new cultivar approximately 35 weeks in age as grown in 2.5-liter containers outdoors in Cambridge, New Zealand. Plants were grown under average day temperatures of 17° to 28° C. and average night temperatures of 8° to 15° C. The phenotype of the new cultivar may vary with variations in environmental, climatic, and cultural conditions, as it has not been tested under all possible environmental conditions. The color determination is in accordance with the 2001 R.H.S. Colour Chart of the Royal Horticultural Society, London, England, except where general color terms of ordinary dictionary significance are used.

General plant characteristics:

*Plant type.*—Perennial shrub.

*Plant habit.*—Bushy, mounded.

*Flowering period.*—From January to March in New Zealand.

*Height and spread.*—Reaches about 80 cm in height and 100 cm in width.

*Hardiness.*—Tolerates temperatures from 2° C. to 35° C.

*Culture.*—Prefers well-drained, lean to moderately fertile soils in full sun to partial shade.

*Diseases and pests.*—Greater mildew resistant than is typically observed for *Hebe* cultivars.

*Root description.*—Fibrous and fine, N176C in color.

Growth and propagation:

*Growth rate.*—Moderate.

*Propagation.*—Terminal stem cuttings.

*Time required for root initiation.*—About 7 to 10 days at 20° C. under mist, bottom heat is not necessary.

*Time required for root development.*—About 70 days fully develop in a 5 cm liner, about 18 weeks to finish in a 2.5 liter container from a 5 cm liner.

Stem description:

*Stem size.*—Lateral branches are 3 to 4 cm in length and 4 to 6 mm in width.

*Stem shape.*—Round.

*Stem color.*—144A becoming N200A when mature.

*Stem surface.*—Smooth with sparse covering of appressed hairs.

*Internode length.*—1.5 to 2 cm.

*Branching habit.*—Freely branched.

*Branching aspect.*—Upright and slightly arching.

Foliage description:

*Leaf shape.*—Lanceolate to oblong.

*Leaf division.*—Simple.

*Leaf base.*—Rounded.

*Leaf apex.*—Broadly acute.

*Leaf venation.*—Only mid rib is conspicuous, 199B on upper surface and 199A on lower surface.

*Leaf margins.*—Entire.

*Leaf attachment.*—Sessile.

*Leaf arrangement.*—Opposite.

*Leaf surface.*—Glabrous and satiny on upper and lower surface, leathery texture.

*Leaf color.*—Upper surface young foliage; 137B, lower surface young foliage; 138B, margin young foliage; 59A, upper surface mature foliage; 137A, lower surface mature foliage; 137C.

*Leaf number.*—10 to 16 per lateral branch.

*Leaf size.*—4 to 5 cm in length and 2 to 2.5 cm in width.

*Leaf aspect.*—Concave, held at about 45° angle to lateral branch.

*Leaf fragrance.*—None.

Flower description:

*Inflorescence type.*—Racemes of single tubular shaped flowers, arranged at terminal and in opposite pairs at nodes.

*Inflorescence size.*—Average of 6.5 cm in length and 2.25 cm in width at center.

*Flower persistence.*—Persistent.

*Flower shape.*—Tubular.

*Flower fragrance.*—None.

*Flower quantity.*—140 to 160 per raceme, 3 to 5 racemes per lateral branch, 15 to 20 racemes per plant in a 2.5 liter container.

*Flower arrangement.*—Packed tightly in a whorl on peduncle with flowers opening from the base towards the apex.

*Flower aspect.*—Held outward.

*Flower fragrance.*—None detected.

*Flower lastingness.*—Racemes bloom for about 4 weeks.

*Flower size.*—Average of 7.8 mm in depth and 5.5 mm in diameter.

*Peduncles.*—Average of 1.75 cm in length below flowers and 1.5 mm in width, 144A in color, surface is covered with appressed hairs, round in shape, held at about a 30° angle to stem.

*Pedicels.*—Average of 3 mm in length and <1 mm in width, 144A in color, surface is glabrous, held nearly horizontal to peduncle.

*Flower buds.*—Elliptical in shape, average of 2 mm in length and 1.5 mm in diameter, 61A in color.

*Calyx.*—Cup-shaped, 2.5 mm in length and 1.5 mm in width.

*Sepals.*—4, lanceolate in shape, margin is entire, apex is acute, base is fused to pedicel, margin is entire, surface is glabrous, color of upper and lower surface is 139A, 2.5 mm in length and 2 mm in width.

*Corolla.*—Funnel-formed with petals fused into tube towards base.

*Petals.*—4, about 7.5 mm in length and 2.5 mm width, lobes ovate in shape, margin is entire, apex is rounded to broadly acute, upper and lower surface is glabrous, color of upper surface when opening and mature; 60C with throat 61A, color of lower surface when opening and mature; 60D, color of both surfaces after fading; 62B with throat 60C.

Reproductive organs:

*Gynoecium.*—1 Pistil, stigma shape is not distinguishable, style is about 3.5 mm in length and 60C in color, ovary is 144A in color.

*Androcoecium.*—1 to 2 stamens, anthers are inverted cordate in shape, about 1 mm in length and width and N79A in color, pollen is minimal in quantity and N155B in color.

*Fruit and seed.*—Seed production has not been observed.

I claim:

1. A new and distinct cultivar of *Hebe* plant named 'Sunset Boulevard' as herein illustrated and described.

* * * * *